US009625397B2

(12) United States Patent
Sun (10) Patent No.: US 9,625,397 B2
(45) Date of Patent: Apr. 18, 2017

(54) ATOMIC-SCALED ELECTRONIC SPECTRUM INFORMATION PURIFICATION (75) Inventor: Changqing Sun, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 1157 days.

(21) Appl. No.: 13/704,923

(22) PCT Filed: Jun. 18, 2010

(86) PCT No.: PCT/SG2010/000230
§ 371 (c)(1),
(2), (4) Date: Dec. 17, 2012

(87) PCT Pub. No.: WO2011/159252
PCT Pub. Date: Dec. 22, 2011

(65) Prior Publication Data
US 2013/0090865 A1 Apr. 11, 2013

(51) Int. Cl.
*G01J 3/00* (2006.01)
*G01N 23/225* (2006.01)
*G01N 23/083* (2006.01)
*G06F 17/00* (2006.01)

(52) U.S. Cl.
CPC ....... *G01N 23/2251* (2013.01); *G01N 23/083* (2013.01); *G06F 17/00* (2013.01)

(58) Field of Classification Search
CPC .... G01N 23/225; G01N 21/31; G01N 21/552; G06F 17/00; G01J 3/02; G01J 3/28; G01J 3/42
See application file for complete search history.

(56) References Cited

U.S. PATENT DOCUMENTS

2002/0037251 A1* 3/2002 Driehuys ........... A61B 5/02755
424/9.3

FOREIGN PATENT DOCUMENTS

GB 1 510 719 A 5/1978
JP 11-23499 A 1/1999

OTHER PUBLICATIONS

S. Aksela, et. al., "Direct experimental determination of atom-molecule-solid binding energy shifts for Sb and Bi" New Journal of Physics, Jun. 2, 2010, pp. 1-8, vol. 12.
G.M. Lamble, et al.,"Characterization of Heavy Metal Incorporation in Calcite by XAFS Spectroscopy" J. Phys. IV France, 1997, p. C2-793 to C2-797, vol. 7.

* cited by examiner

*Primary Examiner* — Abdullahi Nur
(74) *Attorney, Agent, or Firm* — Sughrue Mion, PLLC

(57) ABSTRACT

Disclosed is a method for electronic residual spectroscopy for atomic-scaled surface and sub-surface information purification. The method comprises collecting at least one reference spectrum and a plurality of spectra under various conditions. The background of all the plurality of spectra is then subtracted and the plurality of spectra are normalized. Subtracting the reference spectrum from the normalized plurality of spectra will give atomic-scaled, meaningful information at selected zones.

8 Claims, 7 Drawing Sheets (a)

ATOMIC-SCALED ELECTRONIC SPECTRUM INFORMATION PURIFICATION

CROSS REFERENCE TO RELATED APPLICATIONS

This application is a National Stage of International Application No. PCT/SG2010/000230, filed on Jun. 18, 2010, the contents of all of which are incorporated herein by reference in their entirety.

TECHNICAL FIELD

This invention relates to electronic spectrum (ES) collection and information extraction and refers particularly, though not exclusively, to purification of atomic-scaled spectroscopic information regarding bonds and electrons within selected zones of surfaces, sub-surface regions, defects, impurities and interfaces.

BACKGROUND

Surfaces and interfaces with and without chemical and physical conditioning such as, for example, defect, impurity, adsorption, passivation, alloy and compound formation, have been a key driver in physics, chemistry, and materials sciences. Collecting meaningful information about the dynamics and energetics of bonds and electrons in a selected region at the atomic-scale is important to the understanding what is and will be happening in the specific region. This assists researchers in designing processes and materials to achieve desired functions.

The energetics and dynamics of interatomic bonding and electronic distribution in both real and energy spaces dictate the performance of a material and a functional device. Defects, surface characteristics, impurities, and interfaces are key components of materials interacting with the environment for function realization such as, for example, growth nucleation and catalytic reaction, etc. It has long been a challenge to gaining information, in particular, at the atomic scale in a specifically selected site about the statics (order, nature, length, strength) and the dynamics (formation, dissociation, relaxation and vibration) of bond forming and the associated energetics and kinetics of electron transportation, polarization, localization and densification under varied conditions has long been a challenge. Understanding and grasping with factors controlling the bonding and electronic process has been the pursuit of several generations of the scientific community and such information is of paramount importance.

Figure 1:
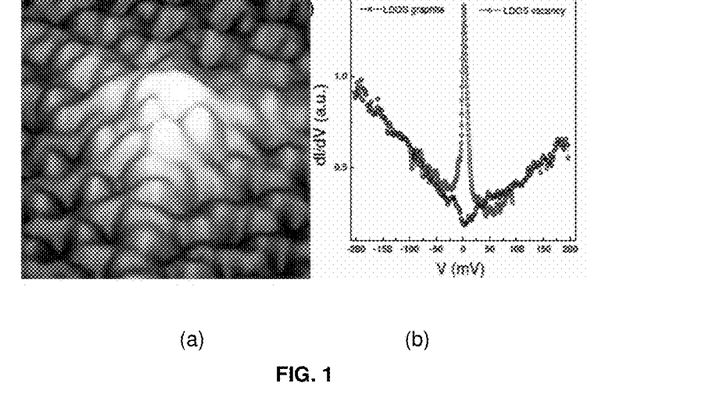

By using a scanning tunneling microscopy/spectroscopy (STM/S) it is possible to obtain an image of an individual atom by probing the flow of charge with energies near the Fermi level under bias crossing the tip and the sample surface of conductors or semiconductors as exampled in FIG. 1. The STM mapped graphite surface and the STS probed energy states of the graphite surface with and without a defect vacancy show that the vacancy exhibits protrusions and Fermi resonant states or Dirac fermions. However, the physical origin is unclear. As such the information obtained is limited only to the top edge of the valence band in energy space and to the top side of the specific surface atom in real space. Therefore, it is difficult to collect information about the bonds and electrons limited to the specific zones of atomic-scaled dimension and electrons with energies beyond the scope of STM/S. Hence, it is hard to determine what is happening to the bonds between the atoms being investigated and those underneath; and what is happening to the local electrons in the valence band and below by using STM/S alone.

Generally, the ES collects information from several nanometers in depth of electrons with energy in the valence band and below, which is determined by the interatomic bonding interaction.

Figure 2:
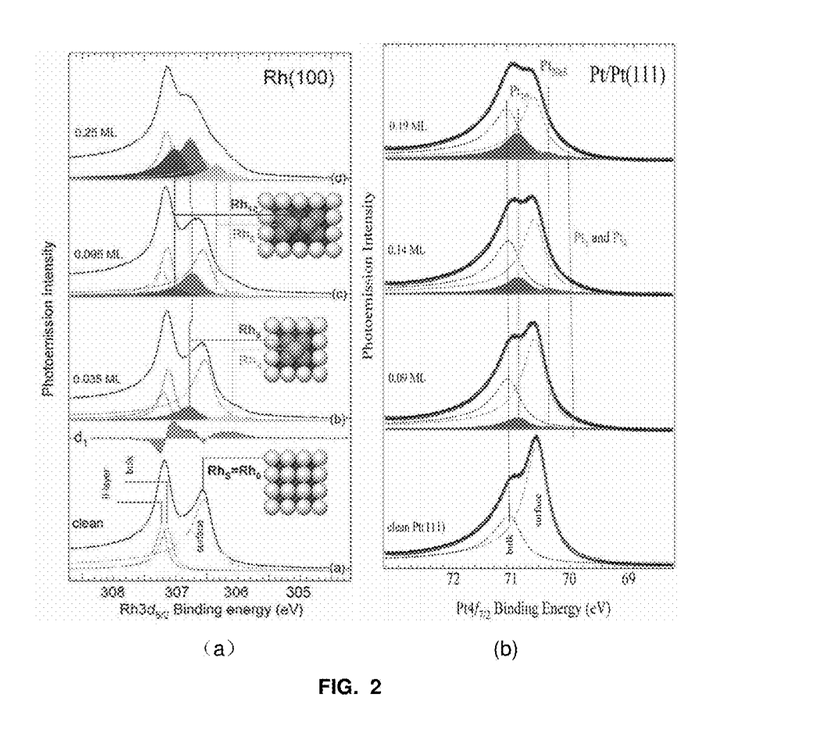
FIG. 2 is a comparison of the raw XPS data for (a) Rh and (a) Pt homogeneously adsorbed adatoms with uncertainty of the number and energies of components in the conventional approach of decomposition.

FIG. 2 compares the raw XPS data for (a) Rh and (b) Pt homogeneously adsorbed adatoms. Traditionally, optoelectronic spectra are analysed by decomposition of the spectra into several components. From the conventional ES data decomposition, it is difficult to gain information of the contribution from the surface before and after physical and chemical conditioning as the signal due to modification is rather weak. Also, uncertainty remains regarding the number and energies of the components in the raw ES data decomposition.

Therefore, gaining atomic-scaled, firmly-defined information of bonds and electrons in the selected zones beyond that which an STM/S can scope, and in the energy window below that which an STM/S can probe, is desirable for materials design and processes control. The selected zones may be in the surface, subsurface, surrounding defect or impurity or bulk interior at the atomic scale within the depth scope of electronic spectroscopy up to several nanometers.

SUMMARY

According to an exemplary aspect there is provided a method for electronic residual spectroscopy for surface and sub-surface information purification. The method comprises collecting at least one reference spectrum and a plurality of spectra under various conditions. The background of all the plurality of spectra is then subtracted and the plurality of spectra are normalized. Subtracting the reference spectrum from the normalized plurality of spectra will give atomic-scaled, meaningful information. Preferably, the residual spectra can then be calibrated and specified.

The at least one reference spectrum may be obtained from a clean and as close to perfect surface as possible. The background may be subtracted using the standard linear or Shelly methodology. By reversing the process the bulk information of the interface, alloy, or compound may be purified by filtering out the surface and defect information. The normalizing of the plurality of spectra may be based on the constraint of spectra area conservation to minimize the effect of surface scattering. The calibration and specifying of the residual spectra is based on physical and chemical knowledge of the bulk. The various conditions may comprise experimental conditions. The experimental conditions may comprise at least one of: emission angle, beam energy, crystal orientation, and temperature. The emission angle may be in the range 0 to 90°. The various conditions may further comprise surface conditions. The surface conditions may comprise at least one of: atomic layer, surface adsorbates, impurities, dopants, surface alloys, adatoms, defects, vacancies, crystal size, surface reconstruction and relaxation, under-coordination, hetero-coordination, tetrahedral-coordination, solid and liquid surface, and catalytic reaction. The meaningful information obtained may comprise at least one of: static information and dynamic information. The static and dynamic information may comprise at least one of: local bond order, length, and strength and the dynamics of bond formation; dissociation, relaxation and vibration; local energy density, atomic cohesive energy, and their evolution; local charge density and energy distribution in the valence band and below; and the dynamics and energetics of charge polarization, transportation, and localization.

BRIEF DESCRIPTION OF THE DRAWINGS

In order that the invention may be fully understood and readily put into practical effect there shall now be described by way of non-limitative example only exemplary embodiments, the description being with reference to the accompanying illustrative drawings.

In the drawings:

FIG. 1(a) is a photograph of an STM mapped graphite surface and (b) is a comparison of the STS probed energy states of the graphite surface with and without at least one vacancy. The vacancy exhibits protrusions and Fermi resonant states or Dirac fermions with a physical origin that remains unclear;

DETAILED DESCRIPTION OF THE EXEMPLARY EMBODIMENTS

The CLS from that of an isolated atom is dominated by the overlap and exchange integrals of the interatomic potential in the Hamiltonian and the specific eigen wave function of the core electrons in the with energy level. The strongly localized eigen wave functions remain unperturbed by coordination environment. Any energetic perturbation in the Hamiltonian of an extended bulk solid will lead to the core level shifting further from that of the bulk. The direction of the shift depends on the perturbation to the potential. The perturbation includes bond contraction, bond nature alteration, charge polarization, and other external stimuli such as pressure and temperature. As the crystal potential at equilibrium corresponds to the bond length and bond energy, the CLS is actually proportional to the cohesive energy per bond. Therefore, the bond strength and the CLS are thus correlated.

According to Goldschmidt-Paulings' rule of bond contraction and the derived bond order-length-strength (BOLS) correlation, bonds become shorter and stronger when the coordination number (z) of an atom is reduced. This spontaneous process of bond contraction not only raises the local charge density but also lowers the bond potential energy; such a local charge densification and quantum trap depression will generates an additional density-of-states (DOS) feature to the lower end of the core band occupied by the deeply and densely trapped core electrons.

The shorter atomic distance and the deeply and densely trapped core charges will polarize the weakly bound non-bonding charge such as the otherwise conducting electrons of metals at the nanoscale and the unpaired dangling bond electrons near the vacancy in graphite or graphene. This polarization will generate the impurity states in the vicinity of Fermi level that can be observed using STM/S.

The inhomogeneous and localized polarization of the unpaired valence charge will partially in turn screen and split the crystal potential and hence generate an extra DOS in the core bands with energy above the bulk component. The joint effect of polarization and entrapment will move the whole band up if the polarization is sufficiently strong.

Figure 3:
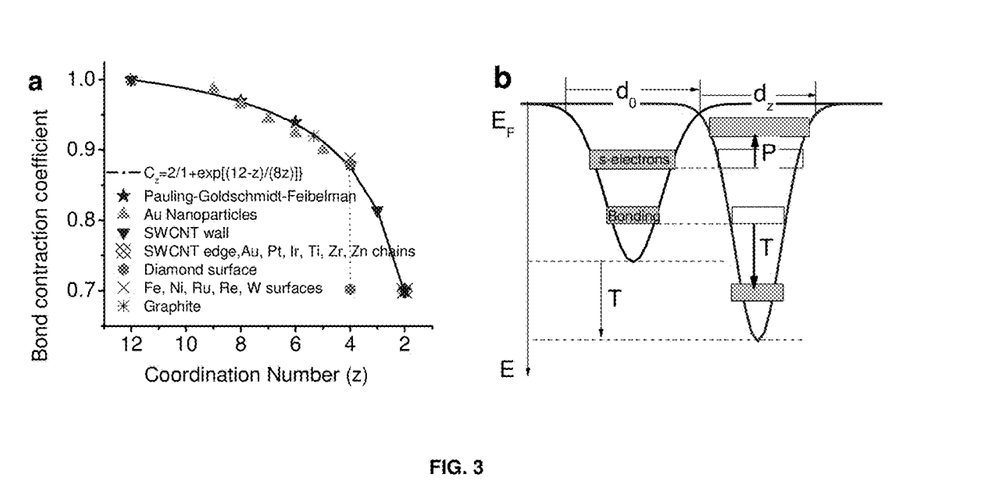
FIG. 3 is an illustration of the undercoordination-facilitated (a) bond contraction, (b) quantum entrapment and the associated core-level shift (CLS) component that is proportional to the energy of bonds between atoms with the particular coordination number (CN) values with the scattered data from various experimental observations.

FIG. 3 illustrates the rule of bond contraction and the derived bond order-length-strength (BOLS) correlation. The atomic undercoordination facilitates local strain ($d_z<d_0$) and quantum trapping (T) of bonding charge and energy, which polarize (P) the otherwise conducting s-electrons or the dangling bond electrons. These T and P processes will split the crystal potential and hence generate extra DOS in the core band. The polarized electrons neither follow the dispersion nor occupy the allowed states defined by the Hamiltonian, instead, they generate states closing to Fermi energy. If the screening is partial, then a P component presents in the XPS spectrum at energy higher than the bulk (B) component and the trapped "final" states partially remain; otherwise, the overall core band spectrum will shift up completely.

Additionally, bond length and energy also change at the heterogeneously-coordinated impurity and interface upon alloy and compound formation, which modifies the chemical environment and hence generates the extra states in the core bands.

Analytically, the CLS can be formulated by the combination of tight-binding approach and the BOLS correlation theory. The single-body Hamiltonian is perturbed by the shorter and stronger bonds facilitated quantum entrapment and the screening effect of polarization, denoted with $\Delta_H$:

$$H(\Delta_H) = -\frac{\hbar \nabla^2}{2m} + V_{atom}(r) + V_{cry}(r)[1 + \Delta_H] \quad (1)$$

where $$1 + \Delta_H = \begin{cases} C_z^{-m} = E_z/E_0 & \text{(Trap depression)} \\ p = (E_v(p) - E_v(0))/(E_v(12) - E_v(0)) & \text{(Polarization)} \end{cases} \quad (2)$$

$$C_z = \frac{d_z}{d_0} = \frac{2}{\left\{1 + \exp\left[\frac{(12-z)}{(8z)}\right]\right\}}$$

The intra-atomic trapping potential, $V_{atom}(r)$, determines the with energy level of an isolated atom, $E_v(0)$. The bulk shift is the gap between the energy of isolated atom and corresponding bulk, $\Delta E_v(12)$ with an effective z vale of 12 rather than 8 for bcc because the involvement of high order atomic coordination numbers. $E_v(x)$ represents the peak energy of the z or P component in the purified ES. $C_z$ is the Goldschmidt-Pauling coefficient of bond contraction. The m is the bond nature indicator, which has been optimized to be unity for metals. The p is the coefficient of polarization to be determined from the ES analysis. Parameters involved are given as follows:

$$\begin{cases} E_v(k) = E_v(0) + \Delta E_v(z) + 2z\beta_z\Phi(z, R, k) & \text{(dispersion)} \\ \Delta E_v(z) = E_v(z) - E_v(0) = \alpha_z + z\beta_z & \text{(core level shift)} \\ \alpha_z = -\langle \varphi_v(r)|V_{cryst}(r)(1+\Delta_H)|\varphi_v(r)\rangle \propto E_z & \text{(exchange integral)} \\ \beta_z = -\langle \varphi_v(r)|V_{cryst}(r)(1+\Delta_H)|\varphi_v(r-d)\rangle \propto E_z & \text{(overlap integral)} \end{cases} \quad (3)$$

Where $\phi_v(r)$ ($r \neq r'$) is the specific Bloch wave function at a specific site. $\Phi(z,R,k) \leq 1$ and $2z\beta_z$ is the maximal band width. The ratio of $\beta_z/\alpha_z < 1/100$ because of the localized nature of the eigen wave function. The z-resolved binding energy for the specific core level could be represented by:

$$\frac{E_v(z) - E_v(0)}{E_v(12) - E_v(0)} = \begin{cases} C_z^{-1} & \text{(Entrapment)} \\ p & \text{(Polarization)} \end{cases} \quad (4)$$

If the polarization-trap coupling effect is apparent, the term $C_z^{-1}$ is replaced by $pC_z^{-1}$, the trapped states will move up closing to the bulk component. This equation provides constraint for the energy separation between components in the XPS data deconvolution and the derivative of the $E_v(0)$ and its bulk shift of $$\Delta E_v(12) = E_v(12) - E_v(0).$$

For the surface without apparent polarization, the following relation:

$$\frac{E_v(z) - E_v(0)}{E_v(z') - E_v(0)} = \frac{C_{z'}}{C_z}, \text{ or, } E_v(0) = \frac{C_{z'}E_v(z) - z'C_z}{C_{z'} - C_z} \quad (5)$$

defines the energy correlation between the components and the direction of the CLS. By taking the average and the standard deviation, the expression for the surface CLS is:

$$E_v(z) = \langle E_v(0) \rangle \pm \sigma + [E_v(12) - Ev(0)]/C_z$$

With the derived z and $E_v(z)$ for each component of fitting, it is possible to derive the coordination-resolved local strain, core level shift (potential trap depth), binding energy density, and the cohesive energy per discrete atom of concern:

$$\begin{cases} \varepsilon(z) = c_z - 1 & \text{(Local strain)} \\ E_v(z) - E_v(0) = \Delta E_v(B)c_z^{-1} & \text{(potential trap depth)} \\ E_d(z) = c_z^{-(m+3)}E_d(12) & \text{(Binding energy density)} \\ E_c(z) = z_{ib}c_z^{-m}E_c(12) & \text{(Atomic cohesive energy)} \end{cases} \quad (6)$$

Where $z_{ib} = z/12$ is the reduced atomic CN and m=1 is the bond nature indicator for metals.

Likewise, surface and interface chemical conditioning also change the bond nature, length and energy, which modifies the Hamiltonian and hence the CLS in terms of entrapment and polarization.

Figure 4:
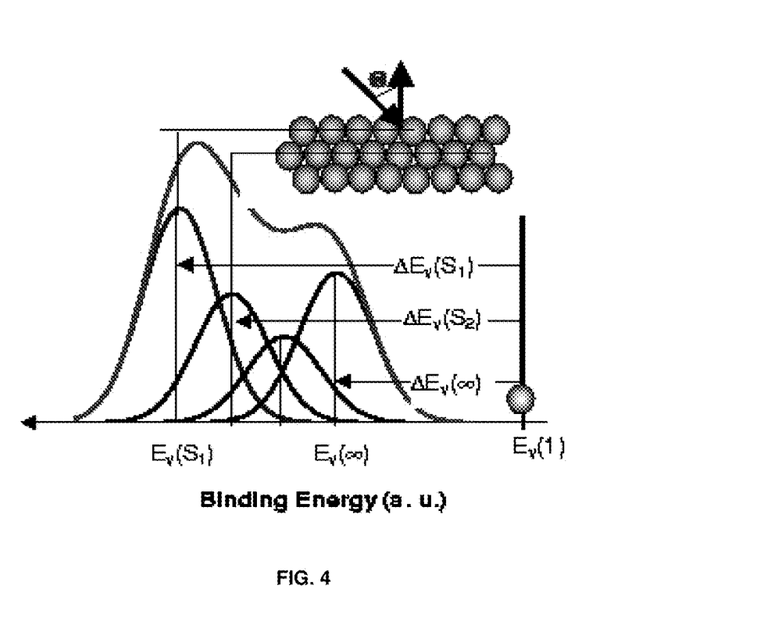
FIG. 4 shows the correspondence between the surface atomic layers ($S_1$, $S_2$, . . . ) and the ES components and the energy separation between the specific component and the energy level of an isolated atom $E_v(1)$, ∞ represents the bulk (B). The intensity of each component varies with the angle between the surface normal and the incident beam or the emission electron beam. The ES collects more surface information at a larger incident beam angle than at a smaller angle.

Electron spectroscopy (ES) is a technique using the light of X-ray, synchrotron radiation, ultraviolet, and energetic electrons to excite electrons inside a crystal. As illustrated in FIG. 4, the penetration depth of the incident beam depends on the beam energy and the angle between the surface normal and the emitted electron beam or the incident radiation beam, called the incident or emission angle. Beams of a smaller emission angle and/or higher energy can penetrate deeper to collect more information from the bulk than beams of larger emission angles and/or lower energy. However, the spectral intensity often includes background information due to artifacts in the experiment. As such the general intensity and component energies will change with the surface and the measurement conditions. Surface modification will lead to extra features. The collecting of information at different depths may be achieved by adjusting the emission angle and/or the beam energy.

This mechanism enables the information from the surface and subsurface region to be purified before and after any process takes place. The process may be one or more of: defect generation, adatom addition, growth, chemical reaction, and adsorption that involves at least two surface layers for bond formation. Therefore, such purification can complement the STM/S that collects information from the top edge of the valence band and the top side of the surface atoms.

After the standard Shirley or linear background subtraction and the spectral area normalization of the collected ES data under the guideline of spectral area conservation, the purified spectra could be obtained by subtracting the spectra collected from surface with edge atoms by the one collected from the clean surface under the same experimental conditions including incident beam energy, temperature, and so forth. The rule of area conservation means that the integration of each spectrum is proportional one to another because the defect scattering will weaken the spectral intensity. Such a process enables the purification of the edge states as it filters out the undesired information. The additional advantage of such a process is the minimization of the influence by extrinsic factors such as the background uncertainty and the "initial-final states" effect that exists throughout the duration of measurement.

The exemplary embodiment provides a method whereby by subtracting from a spectrum collected under specifically varied conditions the standard reference collected from the clear surface at the smallest emission angle and upon background subtraction and spectral area normalization of both the specific and the reference spectra, the obvious artifacts will be removed. The process purifies the meaningful information generated by the experimental or surface condition change. The reverse process can be applied to purify the bulk information of interface, alloy, or compound by filter out the surface and defect information. If N spectra have been collected at different angles ($\theta_i$), atomic-layer-resolved purification can be realized using the relation: $I(\theta_i) - \Sigma' I(\theta_j)/(N-1)$ for different atomic layers (the "'" excludes the term of $\theta_i$). This method enables the extraction of such atomic-scaled information by using the existing facilities of x-ray, ultraviolet light, and electron beam sourced spectroscopy. The spectra can be collected from surface or surface before and after conditioning.

Figure 5:
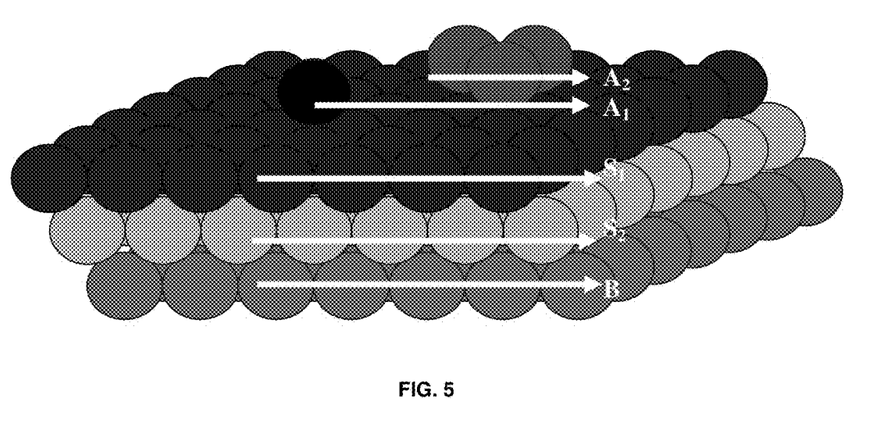
FIG. 5 is an illustration of the surface physical conditioning with irregularly grown adatoms, $A_1$ and $A_2$ with an effective atomic CN smaller than that of the perfect surface. $S_1$, $S_2$ and B represent the outmost, the second and the bulk components. A surface conditioning such as chemisorption involves at least two interatomic spacings.

FIG. 5 illustrates the atomic arrangement at a surface with irregularly grown adatoms denoted with $A_1$ and $A_2$ with effective coordination number (CN) smaller than that of the perfect surface. $S_1$, $S_2$ and B represent the outermost, the second and the bulk components. A surface conditioning such as chemisorption involves at least two interatomic spacings.

Figure 6:
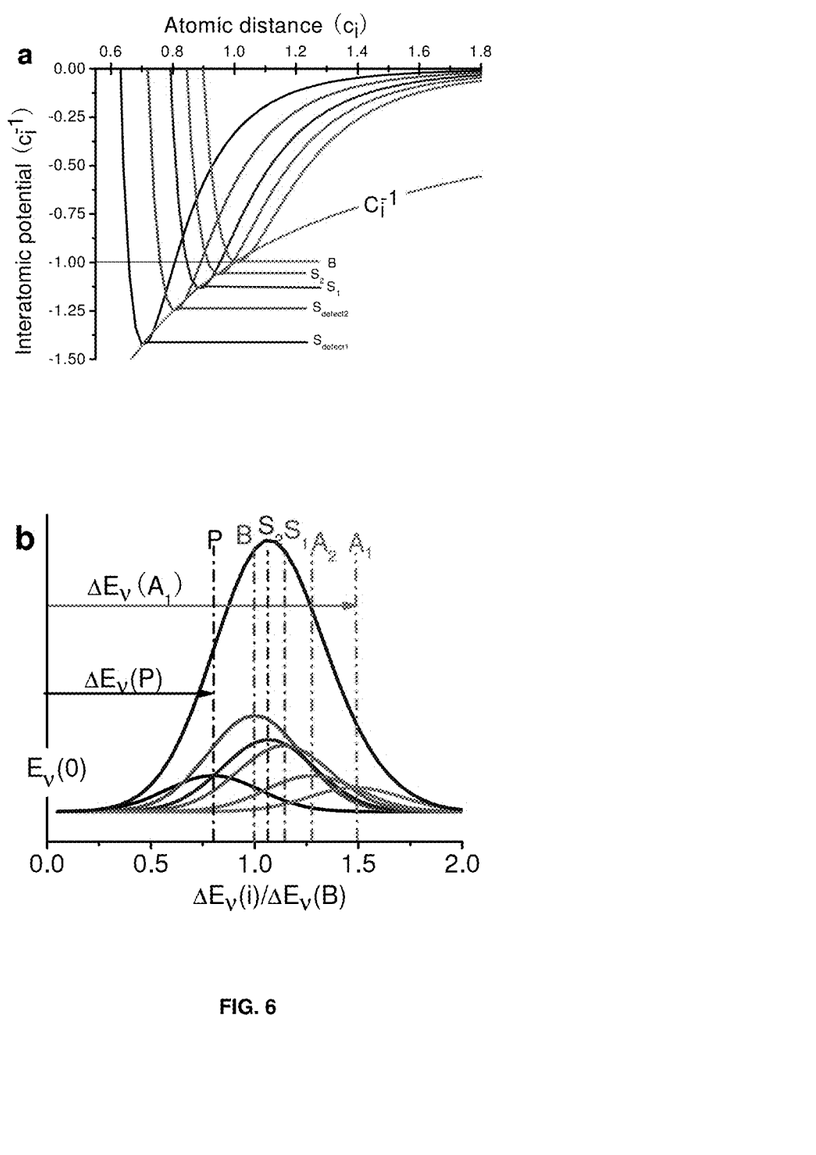
FIG. 6 is an illustration of undercoordination-facilitated (a) local strain ($d_z<d_0$) and quantum entrapment (T) and their correlation between (b) the energy components in the ES spectrum.

FIG. 6 Illustrates the undercoordination-facilitated strain, correlation between the pairing-potential well depths for the adatom- and surface-induced core level shift. (a) These XPS components satisfy the following criteria (b):
1. In addition to the main peaks of B, $S_2$, $S_1$, there should be A and P components representing the trapped and the polarized states of the under-coordinated adatoms.
2. The energy shift should be positive and the lower-z component shifts further. However, the P states should move oppositely with respect to the A states.
3. The energy shift of each component is proportional to the magnitude of bond energy, which follow this relationship:

$$\Delta E_v(i):\Delta E_v(B=12)=E_i:E_b=c_i^{-m}=A, S_1, S_2).$$

By use of the exemplary embodiment it is possible to collect statistics on the atomic scale and obtain useful information on bonds and electrons in the valence band and below. It is also possible to enhance the capacity of existing spectroscopic technologies for monitoring the in situ bonding and electronic processes. These are useful to researchers and industry sectors in the fields of adsorption, catalytic reaction, growth nucleation, alloy and compound formation.

In the exemplary embodiment X-resolved electron residual spectroscopy is used for local bond and electronic information purification at the atomic scale at a specific site. In the exemplary embodiment X may represent one or more of:
1. experimental conditions such as, for example, one or more of: emission angle within the range 0 to 90°, beam energy, crystal orientation, temperature, and mechanical tension or compression; and
2. surface conditions such as, for example, one or more of: atomic layer, surface adsorbates, impurities, dopants, surface alloys, adatoms, defects, vacancies, crystal size, surface reconstruction and relaxation, under coordination, hetero-coordination, tetrahedral coordination, solid and liquid surface, and catalytic reaction.

The exemplary method includes:
1. collecting spectra under various X conditions including at least one reference spectrum obtained from a clean and as close to perfect surface as possible;
2. subtracting the background of all the spectra using the standard linear or Shelly methodology;
3. normalizing the spectra based on the constraint of spectra area conservation to minimize the effect of surface scattering;
4. subtracting the reference spectrum from the X-resolved spectra thereby giving the meaningful information;
5. the residual spectra can then be calibrated and specified based on physical and chemical knowledge of the bulk; and
6. by reversing the process it is possible to purify the bulk information of the interface, alloy, or compound by filtering out the surface and defect information.

The hardware and software used may be known spectroscopy equipment including:
a. X-ray photoelectron spectroscope (XPS);
b. Ultraviolet photoelectron spectroscope (UPS); and
c. Auger electron spectroscope (AES).

Multiple detectors may be installed to simultaneously collect angle-resolved information. The software may include applications for data processing of background subtraction and diffracting.

The information obtained may be static and/or dynamic information including one or more of:
1. local bond order, length, and strength and the dynamics of bond formation, dissociation, relaxation, and vibration;
2. local energy density, atomic cohesive energy, and their evolution; and
3. local charge density and energy distribution in the valence band and below, and the dynamics and energetics of charge polarization, transportation, localization and densification.

EXAMPLES

Figure 7:
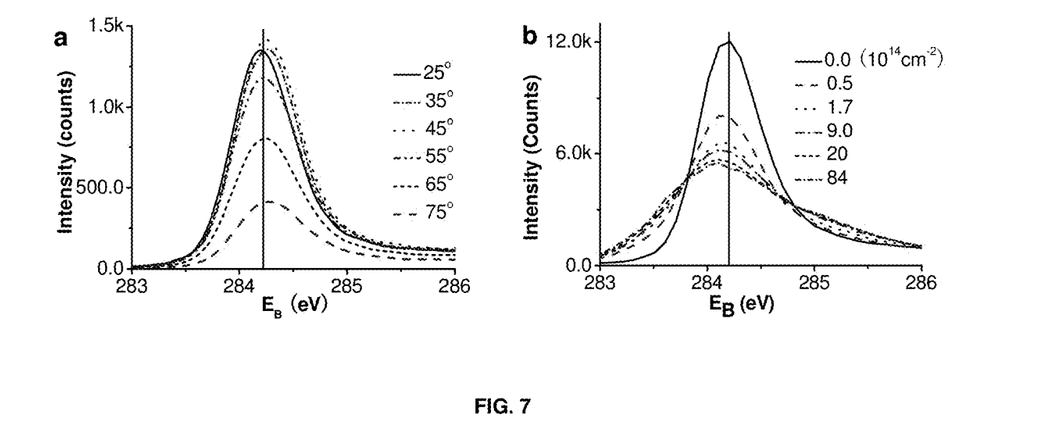
FIG. 7 shows the XPS raw data collected from:
(a) a vacancy-free graphite surface at different emission angles; and
(b) a surface with at least one defect surface at 55° of different $Ar^+$ spray doses.

FIG. 7 shows the raw XPS spectra collected at room temperature from graphite surface (a) at different emission angles and from (b) graphite vacancy surface at 55° at different doses of $Ar^+$ spray. From the raw spectra, it is difficult to extract information of concern.

Figure 8:
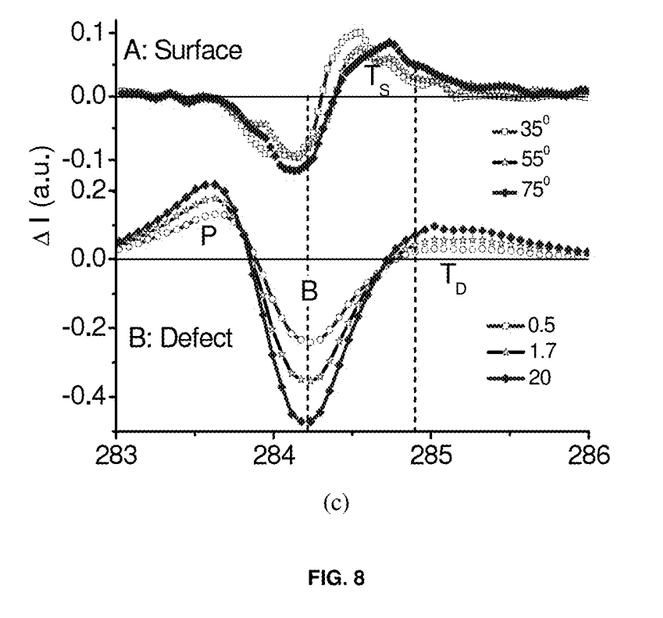
FIG. 8 is a comparison of the purified XPS C 1s data (in FIG. 7) showing A: the trapped ($T_S$) surface states, B: the trapped ($T_D$) and the polarized (P) defect states and their evolution upon defect density increasement with clarification of the physical origin of the STM/S resolved protrusions and Dirac fermions in FIG. 1.

However, a purification using the invented method as shown in FIG. 8 has resulted in clear information with the additionally resolved components. The valleys correspond to the bulk component. The surface shows only one extra peak denoted as $T_S$ that moves to lower energy as the emission angle is increased. As defects are generated, the $T_S$ evolves into $T_D$. The $T_D$ is accompanied by the presence of P component and the Dirac fermions. As the defect density is increased, the $T_D$ intensity grows and the P moves up in both energy and intensity. Therefore, the $T_D$, the P, and the Dirac fermions are correlated as a whole to the undercoordinated defect atoms. An atomic-scaled spectroscopic purification revealed two extra C-1s states as the consequence and origin of graphitic Dirac fermions—polarization of the dangling-bond electrons by the undercoordination-facilitated quantum entrapment and densification of the energetically low-lying electrons.

Figure 9:
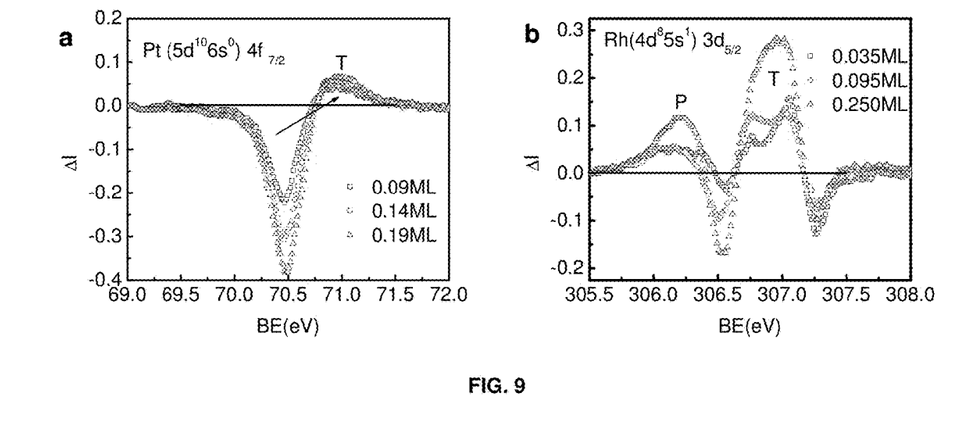
FIG. 9 shows the purified XPS spectra (in FIG. 2) with clearly-resolved trapped (T) states for Pt and (d) the T and polarized (P) states for Rh with clarification of the charge flow direction between the reactant and the catalyst in the process of catalytic reaction, which explain why Rh is good for hydrogenation (reduction) and Pt is good for oxidation.

Likewise, FIG. 9 shows the (a) trapped (T) states for Pt and (b) the T and polarized (P) states for Rh adatoms purified from the spectra given in FIG. 2.

FIG. 2

By use of the exemplary embodiment the use of such a process may be removed, and may provide an increased level of certainty in the specification. It may also provide clearer and more comprehensive information by removing the bulk information. FIGS. 2 (a) and (b) show the uncertainty in the number, energy, and direction of the components while the purified states FIGS. 9 (a) and (b) show clearly the trapped and the polarized states with clarification of the charge flow direction between the reactant and the catalyst in the process of catalytic reaction. The findings explain why Rh is good for hydrogenation (reduction) and Pt is good for oxidation.

Figure 10:
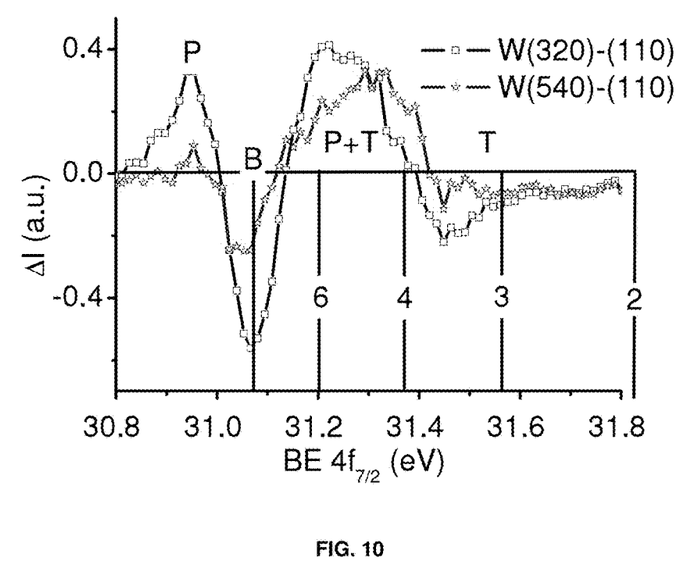
FIG. 10 shows the purified T and P states for W(110) vicinal edge atoms from the raw XPS data, suggesting that undercoordinated W atoms could be a candidate of donor-type catalyst.

FIG. 10 illustrates the purified tungsten edge atom states with the trap (T), polarization (P) and their joint effect of (P+T), being substantially the same as that of the undercoordinated Rh adatoms in FIG. 9. Therefore, undercoordinated W edge atoms could be a potentially efficient catalyst.

Figure 11:
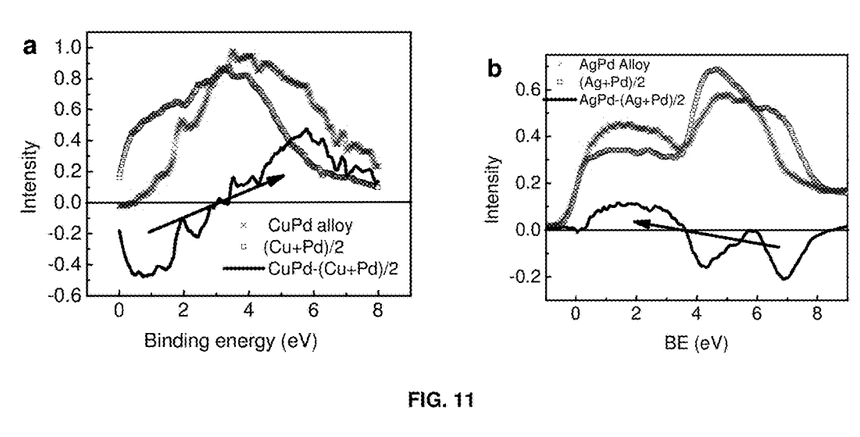
FIG. 11 shows the residual spectra for (a) the CuPd and (b) AgPd alloys with the direction of valence charge migration within the valence band upon alloy formation indicated by the arrows. The opposite directions of valence polarization may distinguish the CuPd from the AgPd that may serve as a charge acceptor and donor respectively in catalytic reaction.

FIG. 11 shows the purified spectra for (a) the CuPd and (b) AgPd alloys with identification of the direction of valence charge migration within the valence band upon alloy formation being indicated by the arrows. The opposite directions of valence polarization may distinguish the CuPd from the AgPd that may serve as a charge acceptor and donor respectively in catalytic reaction.

By focusing on the purification of the meaningful information by zooming into the atomic scaled zones in the surface, subsurface and interface region regarding the bond (order, length, energy) as well as the core and bonding electrons both statically and kinetically, more information may be obtained than would have been obtainable by using STM/S, x-ray, ultraviolet photoelectron, or Auger electron spectroscopy, alone. By using the method of the exemplary embodiment more information may be obtained to provide guideline for materials design and functional modification. This is required of defects, impurities, interfaces, surfaces and catalytic research; as well as in the chemical industry. It is able to provide in situ information about one or more of: crystal growth, surface adsorption, surface passivation and nanostructure formation.

Whilst the foregoing description has described exemplary embodiments, it will be understood by those skilled in the technology concerned that many variations in details of design, construction and/or operation may be made without departing from the present invention.

The invention claimed is:

1. A method for electronic residual spectroscopy information purification for obtaining atomic-scaled, meaningful information of a surface and sub-surface of a sample, the method comprising: collecting at least one reference spectrum, wherein the at least one reference spectrum is from a clean and as close to perfect surface as possible; collecting a plurality of spectra from the surface of the sample under varied conditions; subtracting a background from all the plurality of spectra; normalizing the plurality of spectra; and subtracting the reference spectrum from the normalized plurality of spectra to give the meaningful information.

2. A method as claimed in claim 1, wherein the background is subtracted using the standard linear or Shirley methodology.

3. A method as claimed in claim 1, wherein the normalizing of the plurality of spectra is based on a constraint of spectra area conservation to minimize effect of surface scattering.

4. A method as claimed in claim 1, further comprising calibrating and specifying residual spectra based on physical and chemical knowledge of the sample.

5. A method as claimed in claim 1, wherein the varied conditions comprise experimental conditions, the experimental conditions comprising at least one selected from the group consisting of: emission angle, beam energy, crystal orientation, and temperature.

6. A method as claimed in claim 5, wherein the emission angle is in the range 0 to 90°.

7. A method as claimed in claim 5, wherein the varied conditions further comprise surface conditions, the surface conditions comprising at least one selected from the group consisting of: atomic layer, surface adsorbates, impurities, dopants, surface alloys, adatoms, defects, vacancies, crystal size, surface reconstruction and relaxation, under-coordination, hetero-coordination, tetrahedral-coordination, solid and liquid surface, and catalytic reaction.

8. A method as claimed in claim 1, wherein the meaningful information obtained comprises at least one of: static information and dynamic information; the static and dynamic information comprising at least one selected from the group consisting of: local bond order, length, and strength and the dynamics of bond formation, dissociation, relaxation and vibration; local energy density, atomic cohesive energy, and their evolution; local charge density and energy distribution in the valence band and below; and the dynamics and energetics of charge polarization, transportation, localization and densification.

* * * * *